United States Patent [19]

Csanitz et al.

[11] 4,437,971
[45] Mar. 20, 1984

[54] ELECTROCHEMICAL OXYGEN SENSOR, PARTICULARLY FOR EXHAUST GASES FROM COMBUSTION ENGINES

[75] Inventors: Herbert Csanitz, Bietigheim-Bissingen; Helmut Weyl, Schwieberdingen, both of Fed. Rep. of Germany

[73] Assignee: Robert Bosch GmbH, Stuttgart, Fed. Rep. of Germany

[21] Appl. No.: 275,518

[22] Filed: Jun. 19, 1981

[30] Foreign Application Priority Data

Jun. 21, 1980 [DE] Fed. Rep. of Germany ....... 3023337

[51] Int. Cl.³ .......................................... G01N 27/46
[52] U.S. Cl. .................................. 204/427; 204/421; 204/424; 204/428; 123/536; 123/568
[58] Field of Search ................ 204/1 S, 1 B, 195 S, 204/195 R, 421, 424–429

[56] References Cited

U.S. PATENT DOCUMENTS

| | | | |
|---|---|---|---|
| 3,043,764 | 7/1962 | Harvey | 204/1 B |
| 3,464,008 | 8/1969 | Meysson et al. | 204/195 S |
| 3,883,408 | 5/1975 | Kim et al. | 204/195 S |
| 4,046,712 | 9/1977 | Cairns et al. | 252/466 PT |
| 4,116,797 | 9/1978 | Akatsuka | 204/195 S |
| 4,172,247 | 10/1979 | Ikeura | 204/195 S |
| 4,175,019 | 11/1979 | Murphy | 204/195 S |
| 4,212,273 | 7/1980 | Maruoka | 204/195 S |

FOREIGN PATENT DOCUMENTS

620881 8/1978 U.S.S.R. .......................... 204/195 S

Primary Examiner—T. Tung
Attorney, Agent, or Firm—Frishauf, Holtz, Goodman & Woodward

[57] ABSTRACT

To prevent signal degradation of a sensing element, which may be a potentiometric or a polarographic sensor, having a reference electrode exposed to ambient air, the reference electrode (22) is placed within a chamber (21) which has included therein granules (39) of a material inert with respect to oxygen and having a surface hardness at least as hard as the reference electrode (22) so that, upon subjection of the sensor, when coupled to the exhaust system of an internal combustion engine, to vibrations, shocks and jolts, the granules will move in the chamber, rub against the electrode, and hence keep the electrode surface activated and free from contamination which may have penetrated with ambient air.

14 Claims, 1 Drawing Figure

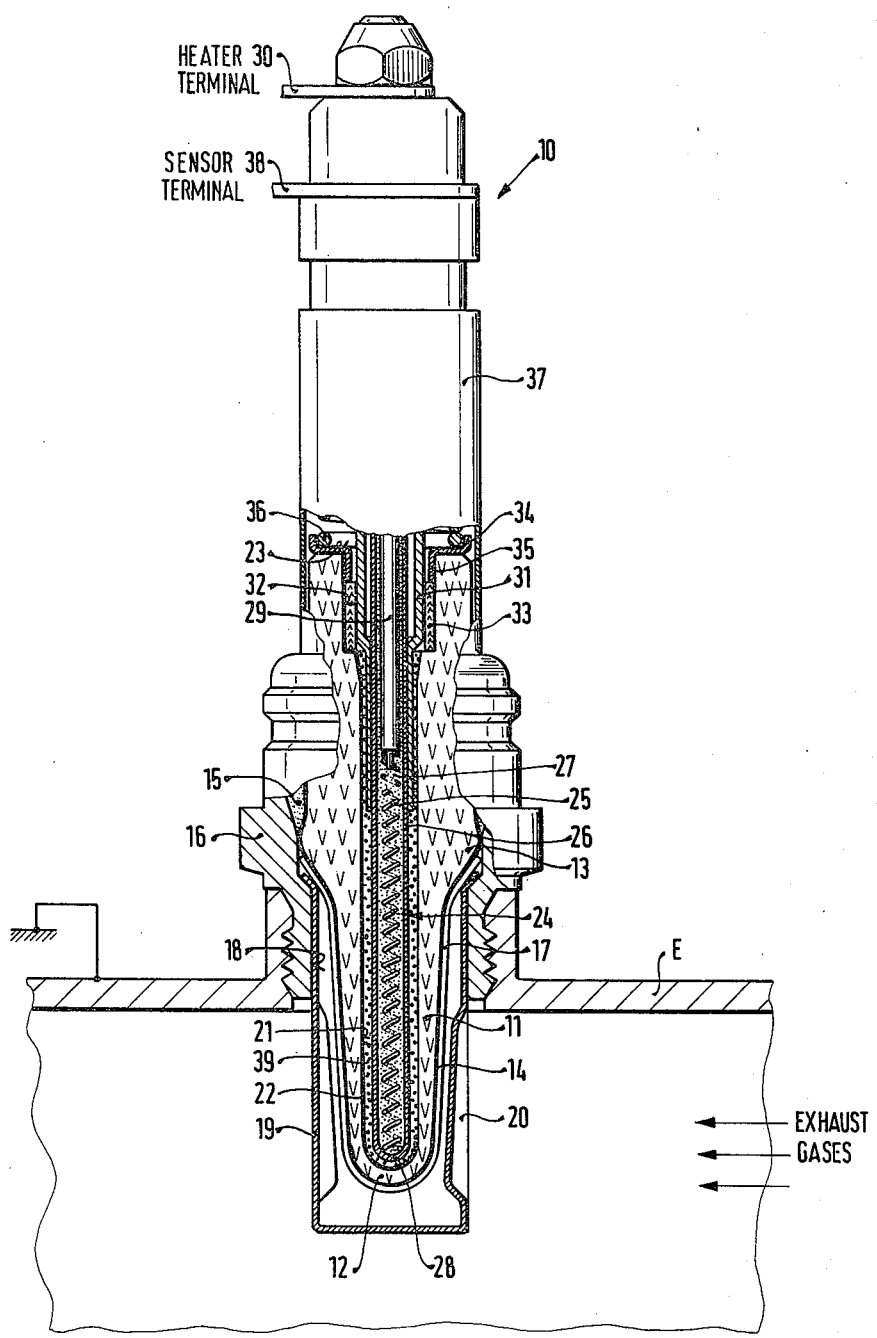

ELECTROCHEMICAL OXYGEN SENSOR, PARTICULARLY FOR EXHAUST GASES FROM COMBUSTION ENGINES

Reference to related publications, applications, and patents, assigned to the assignee of the present application:

German Disclosure Document DE-OS No. 23 44 245, FRIESE and POLLNER;

U.S. Ser. No. 121,632, filed Feb. 14, 1980, now U.S. Pat. No. 4,282,080, MULLER et al, U.S. Pat. No. 4,212,720, filed June 27, 1978, MAURER ET AL, published: DE:OS No. 27 32 743; GRUNER ET AL, U.S. Pat. No. 4,219,399, filed Sept. 10, 1979;

U.S. Ser. No. 213,049, filed Dec. 4, 1980, DIETZ now U.S. Pat. No. 4,356,065.

The present invention relates to an electrochemical sensor, and more particularly to a sensor in which an oxygen ion conductive solid electrolyte has two porous electrodes applied thereto, one of which being a reference electrode, which is located within a hollow space or a chamber to which oxygen from ambient air is supplied.

BACKGROUND

Various types of oxygen sensors have been proposed; in one such construction, a solid electrolyte, essentially tubular element in which the tube is closed at one end, has an outer sensing electrode exposed to the test gases, typically exhaust gases from an internal combustion (IC) engine applied thereto; a second electrode is located at the inner portion of the hollow tubular element, which is exposed to air, the oxygen of which forms a reference gas with respect to oxygen content in the exhaust gases from the IC engine. Preferably, the outer electrode is catalytically active (see German Patent Disclosure Document DE-OS No. 23 44 245, for example).

It has been found that, in use, a certain shift in the signal voltages will result, particularly in a direction to lower signal voltage levels. If such a sensor is included in an automatic fuel-air mixture control system, optimum supply of fuel to the IC engine may be impaired. The sensors may, in cross section, be essentially ring-shaped; the space to which the reference electrode, that is, the electrode exposed to the oxygen of ambient air is placed, need not be cylindrical or quasi-cylindrical, however; the space or chamber may have any other cross section, for example rectangular—see U.S. application Ser. 121,632, filed Feb. 14, 1980 now U.S. Pat. No. 4,282,080 Muller et al. The chamber, further, may retain a heating element therein, see for example the aforementioned U.S. application Ser. No. 121,632, now Patent 4,282,080 Muller et al U.S. Pat. No. 4,212,720, filed June 27, 1978 or U.S. Pat. No. 4,219,399, filed Sept. 10, 1979 Sensors may operate in accordance with the potentiometric principle, that is, similar to a fuel cell, or according to the polarographic principle (see U.S. application Ser. No. 213,049, filed Dec. 4, 1980, DIETZ, now U.S. Pat. No. 4,356,065).

THE INVENTION

It is an object to improve the construction of the sensor so that the signal voltages derived therefrom will be essentially constant during the life of the sensor.

Briefly, the space in which the reference electrode is located retains movable granules or tiny pellets of a material which is inert with respect to oxygen and at least as hard as the reference electrode. Usually, the reference electrode is applied in form of a thin layer on the solid electrolyte body, for example made of platinum, and the granules, grains or pellets, preferably are of aluminum oxide, stabilized zirconium dioxide, magnesium spinel, or silicates, having a grain size of between 0.02 and 1 mm diameter. The chamber may be filled almost entirely with the granules, or may contain as little as a few percent of the hollow space defined thereby which are filled with granules.

It has been found that, in operation, ambient air which supplies the reference oxygen contains contaminants which can deposit on the surface of the reference electrode and thus diminish its activity; vibration which occurs in the normal operation of an internal combustion engine, with which the sensor is primarily adapted to be associated, shakes the granules within the hollow chamber, thus effecting cleaning action of the electrode. Normally, the sensor would be screwed into a portion of the exhaust system, for example the exhaust manifold or an exhaust pipe, all subject to vibration, so that self-cleaning of the reference electrode is effected during operation of the engine.

The sensor has the advantage that the output signal derived therefrom will not deteriorate with age of the sensor, while additionally protecting the reference electrode against contamination or dirt which might penetrate into the sensor.

DRAWING

The single FIGURE is a part-sectional, part-side view of a sensor, to a scale enlarged with respect to an actual construction, and arranged to operate according to the polarographic measuring principle.

The sensor shown in the FIGURE is, generally, similar to that described in the referenced Patent 4,212,720, but differs therefrom in that the sensor there described is a potentiometric sensor, whereas the sensor shown herein operates according to the polarographic principle and, additionally, includes the features of the present invention.

The sensor 10 has a solid electrolyte tube 11, made of stabilized cubic zirconium dioxide. The end thereof which extends into the exhaust pipe—not shown—of an internal combustion engine has a closed integrally formed bottom wall 12. The outer side of the closed tube 11 is formed with a flange 13. A layer-like measuring or sensing electrode 14 is coated to the outside of the solid electrolyte tube. The electrode 14 is porous and preferably catalytically active. In a preferred form, the measuring electrode 14 consists of a layer of platinum of about 0.01 mm thickness, and extends, at least in form of a conductive track, over the flange 13 of the solid electrolyte tube, where it is in contact with an electrically conductive sealing mass 15, for further connection to a metallic housing 16 which, for example, may be part of the housing of the sensor which is connected to ground or chassis of the motor vehicle. This construction is generally known.

The sensing electrode 14 is covered with a diffusion barrier 17, that is, a barrier which prevents free ingress of oxygen molecules to the sensing electrode. This diffusion barrier 17 extends preferably over the entire region of the solid electrolyte tube 11, exposed to the sensing gas. A typical diffusion barrier is about 0.4 mm thick and porous. For a specific disclosure of such a diffusion barrier 17, limiting the application of oxygen molecules to the sensing electrode, reference is made to U.S. application Ser. No. 213,049, filed Dec. 4, 1980, DIETZ, now U.S. Pat. No. 4,356,065. The solid electrolyte tube 11 is secured in a longitudinal bore or opening 18 of the housing 16, and sealed therein, as described in the aforementioned U.S. Pat. No. 4,212,720. Housing 16 has a protective tube 19 attached thereto which surrounds the end portion of the solid electrolyte tube 11, with clearance, and is formed with openings 20 to permit access of gas to be measured to the diffusion barrier 17.

A reference electrode 22 is applied to the interior surface of the solid electrolyte tube facing the hollow space or chamber 21 therein. Preferably, the reference electrode 22 is also made of platinum, has a thickness of about 0.01 mm, and is porous. It is carried up to the connecting end surface 23 of the solid electrolyte tube 11.

The inner clearance of the chamber or space 21 is approximately 5 mm. Coaxially located therein is a heating element 24, secured spaced from the surface of the inner walls defining the space 21. The heater element 24, as described in the aforementioned U.S. Pat. No. 4,212,720, includes a resistance wire spiral 25, located within a thin-walled metal sleeve 26 and surrounded by an electrically insulating but good heat conductive powder 27, for example magnesium oxide. The end of the resistance wire 25 close to the solid electrolyte bottom wall 12 is connected to the bottom 28 of the metal sleeve 26 by welding. The other end terminal of the resistance wire 25 is welded to a connecting bolt 29 which extends into the open-end portion of the metal sleeve 26 and is electrically connected to a terminal 30 having a terminal flag or strip. The metal sleeve 26 of the heater element 24 is connected to the housing 16, which is adapted to be connected to the ground or chassis connection of the vehicle, over a metallic intermediate sleeve 31. Sleeve 31 simultaneously secures the heater sleeve in the space 21 of the solid electrolyte tube 12. Reference, again, is made to U.S. Pat. No. 4,212,720 for constructional details in connection therewith.

The hollow space 21 of the solid electrolyte tube is formed with an enlargement 32 at the outer end portion thereof. The enlargement 32 surrounds the sleeve 31, with a little clearance. A ceramic sleeve 33, of electrically non-conductive material, is seated in the enlarged opening. The ceramic sleeve functions as a separator. The ceramic sleeve separator 33 is held in position by a metallic disk 34 having a tubular extension 35, so that the sleeve 33 is reliably positioned in the enlarged portion 32 of the hollow space. The disk 34, which has an upstanding rim at the outside, additionally functions as a contact element for the reference electrode 32 and is pressed by a compression spring 36 against the end face 23 over which the inner reference electrode 22 extends, to form an electrical contact therewith. The compression spring 36 is connected to an electrical contact strip or rail 38 by various internal portions hidden by the metal covering 37; reference is made to the aforementioned U.S. Pat. No. 4,212,720 for constructional details.

In accordance with the present invention, movable grains, granules, or small pellets 39 are positioned in the remaining space of the chamber 21 between the tubular heating element 24 and the inner wall of the solid electrolyte tube 11. These elements 39, which are herein referred to as granules, are inert with respect to oxygen and have a hardness which is at least as great as that of the surface of the reference electrode 22 with which they are in contact. The granules 39 are made of aluminum oxide and have a particle size of between 0.02 and 0.2 mm. The degree of filling of the space depends on the intended position of the sensor 10 within the exhaust tube or other element with which it is to be assembled in the gas stream from an engine. In one example, the filling can take up 95% of available space; it is not critical, however, and varies between a few percent of the volume up to almost 100% thereof. The granules 39 may be made of various materials; rather than using aluminum oxide, other materials are suitable, for example stabilized zirconium dioxide, magnesium spinel, and silicates. Sensors 10 of this type are frequently installed in various pipings and tubings or manifolds carrying hot exhaust gases and coupled to an internal combustion engine. The vibrations, shocks and jolts to which the engine is subjected also are transferred to the sensor. The granules, thus, are shaken within the hollow space, which they do not fill entirely, and thus the granules will have surface rubbing contact with the surface of the reference electrode 22 to cause slight roughening thereof and thus effect continuous cleaning reactivation of the reference electrode 22.

The granules 39 can also be used in sensors of the type in which no heating element is included in the hollow space. For such units, the size of the granules can be up to about 1 mm in diameter.

Other types of heater elements than the ones may be used; for example, rather than using a heater element 24 within a metal sleeve 26, heater elements can be used in which a spiral heater wire is wound on an insulator centrally positioned in the space 21, and without any external metal housing or shield. For such applications, the granules 39 preferably are filled to a filling degree of almost 100%, since they then will have to not only functions as cleaning elements, but additionally have to transfer heat from the heating element to the solid electrolyte tube 11. Reference is made to U.S. Pat. No. 4,219,399.

Heater elements may also be used which are applied in form of layers directly on the solid electrolyte, rather than using resistance wire heater spirals, using wire spirals 25. Layer-like heater elements are used, preferably, in sensors which have a plate-like solid electrolyte, and in which the hollow space over the reference electrode has an essentially rectangular cross section—see, for example, the referenced application U.S. Ser. No. 121,632 now U.S. Pat. No. 4,282,080.

The sensor as described operates in accordance with the polarographic principle if the electrode 38 and the housing are connected to a source of reference voltage, for example in the order of about ½ to 1½ V, and the current is measured in a measuring loop. The current then will be a measure of the oxygen content of the sensing gas to which the outer or measuring electrode 14 is exposed. The structure of the present invention is also suitable for sensors which operate in accordance with the potentiometric principle; in that case, however, the diffusion barrier 17 is omitted and, rather, a porous protective layer is applied over the measuring or sensing electrode 14. Such a porous protective layer may, for example, be made of magnesium spinel.

Various changes and modifications may be made; rather than using a porous ceramic tube 33 as a separator to prevent loss of granules 39 from the space 21 within the solid electrolyte tube, other and equivalent means may be used, such as fine mesh, ceramic or glass fibers, or the like. It is also not necessary that the solid electrolyte body be in the shape of a closed tube; rather, a plate-like solid electrolyte can be used, in which the measuring electrode and the reference electrode are located at specific discrete surface regions, and the reference electrode is placed in a hollow space or chamber accessible to oxygen from ambient air.

We claim:

1. In combination with an exhaust system of an internal combustion engine having an exhaust component (E) subject to vibration,
   an electrochemical sensor to determine the oxygen content of gases, particularly of exhaust gases from an internal combustion engine, said sensor having
   a body (11) of solid electrolyte material;
   a layer-like porous measuring electrode (14) applied to a first surface region of the body;
   means including another surface region of the body defining a hollow chamber (21);
   a layer-like reference electrode (22) located on said other surface region of the body and positioned within the hollow chamber (21), said hollow chamber being open to ambient air, the oxygen of which providing a reference gas;
   and comprising
   movable granules (39) loosely retained and located in at least part of said hollow chamber (21) in which the layer-like reference electrode (22) is located, said granules being inert with respect to oxygen and having a surface hardness which is at least as great as that of the layer-like reference electrode (22).

2. Sensor according to claim 1, wherein the volume of the chamber (21) is taken up by the volume of the granules (39) from several percent of the chamber volume to almost, but not reaching, 100% of the chamber volume.

3. Sensor according to claim 2, wherein the average diameter of the granules (39) is between 0.02 and 1 mm.

4. Sensor according to claim 3, wherein the granules (39) comprise a material selected from the group consisting of: aluminum oxide; stabilized zirconium dioxide; magnesium spinel; and a silicate.

5. Sensor according to claim 4, including closure means (33) closing off said chamber and retaining said granules in the chamber, and including a material pervious to oxygen in ambient air.

6. Sensor according to claim 5, wherein said closure material comprises at least one of: mesh; a sintered element; a porous ceramic body; and ceramic fiber material.

7. Sensor according to claim 6, further including an electrical heater element (24) positioned within said chamber and spaced from the reference electrode (22);
   and wherein the granules are smaller than the space between the heater element (24) and the said other surface region of the solid electrolyte body (11) to which the reference electrode (22) is applied.

8. Sensor according to claim 1, wherein the average diameter of the granules (39) is between 0.02 and 1 mm.

9. Sensor according to claim 1, wherein the granules (39) comprise a material selected from the group consisting of: aluminum oxide; stabilized zirconium dioxide; magnesium spinel; and a silicate.

10. Sensor according to claim 1, including closure means (33) closing off said chamber and retaining said granules in the chamber, and including a material pervious to oxygen in ambient air.

11. Sensor according to claim 10, wherein said closure material comprises at least one of: mesh; a sintered element; a porous ceramic body; and ceramic fiber material.

12. Sensor according to claim 1, further including an electrical heater element (24) positioned within said chamber and spaced from the reference electrode (22).

13. Sensor according to claim 12, wherein the granules are smaller than the space between the heater element (24) and the said other surface region of the solid electrolyte body (11) to which the reference electrode (22) is applied.

14. Sensor according to claim 1, wherein said exhaust component comprises a gas duct system, wherein said sensor is installed to pass through the duct system, vibration of the engine, in operation, causing movement of said movable granules (39) within the chamber (21) and hence rubbing contact of said granules with the reference electrode (22) to clean the surface of the reference electrode and maintain it in activated condition.

* * * * *